United States Patent [19]

Andrews et al.

[11] Patent Number: 5,420,312

[45] Date of Patent: May 30, 1995

[54] GLYCIDYL ETHER FROM ALCOHOL AND EPICHLOROHYDRIN

[75] Inventors: Christopher M. Andrews, Cambridge; Bryan Dobinson, Duxford; William M. Rolfe, Haverhill; Michael R. Thoseby, Cambridge, all of England

[73] Assignee: Ciba-Geigy Corporation, Ardsley, N.Y.

[21] Appl. No.: 979,011

[22] Filed: Nov. 20, 1992

[30] Foreign Application Priority Data

Nov. 23, 1991 [GB] United Kingdom ............... 9125116

[51] Int. Cl.⁶ ............... C07D 301/28; C07D 303/12; C07D 303/27
[52] U.S. Cl. ............................ 549/516; 523/400
[58] Field of Search .................. 549/516, 514, 511

[56] References Cited

U.S. PATENT DOCUMENTS

| | | | |
|---|---|---|---|
| 3,033,803 | 5/1962 | Price et al. ............................. | 260/2 |
| 4,284,574 | 8/1981 | Bagga .................................. | 260/348.43 |
| 4,417,033 | 11/1983 | Bowditch ............................... | 525/481 |
| 4,810,808 | 3/1989 | Tomita et al. ......................... | 549/516 |
| 5,162,547 | 11/1992 | Roth et al. ............................. | 549/516 |

FOREIGN PATENT DOCUMENTS 0491529 6/1992 European Pat. Off. .
0495339 7/1992 European Pat. Off. .

OTHER PUBLICATIONS

Chemical Abstract vol. 104, 1986, 104:208248k.
Chemical Abstract vol. 111, 1989, 111:135434a and Chemical Abstracts 12th Collective Index-formula.

*Primary Examiner*—Joseph E. Evans
*Attorney, Agent, or Firm*—William A. Teoli, Jr.

[57] ABSTRACT

A process for the production of glycidyl ether of an aliphatic, cycloaliphatic or araliphatic primary or secondary alcohol, comprising:

A) reacting epichlorohydrin with a molar excess of the alcohol in the presence of a Lewis acid catalyst; optionally B) dehydrochlorinating the product so obtained; and C) reacting the product from step A) or B) with a molar excess of epichlorohydrin in the presence of alkali and a phase transfer catalyst, and then isolating the glycidyl ether product so obtained.

27 Claims, No Drawings

GLYCIDYL ETHER FROM ALCOHOL AND EPICHLOROHYDRIN

The present invention relates to a chemical process, in particular a process for the glycidylation of aliphatic or cycloaliphatic primary or secondary alcohols.

The reaction of alcohols with epichlorohydrin to produce glycidyl compounds is well known.

Many variations of the basic reaction have been performed in attempts to improve the yield of the desired glycidyl compound, while avoiding the production of undesired by-products.

One known modification involves effecting the reaction using an excess of epichlorohydrin, and performing the reaction in the presence of an alkali, typically an alkali metal hydroxide such as sodium hydroxide, and a phase transfer catalyst. Examples of phase transfer catalysts are tetra-alkylammonium halides such as methyltrioctylamnionium chloride, methyltridecylammonium chloride and tetramethylammonium chloride; and tertiary amine or quaternary ammonium bases such as benzyltrimethylammonium hydroxide. This process technique suffers, however, from low yields (based on epichlorohydrin) and from the formation of polymeric by-products.

Another known technique is to conduct the alcohol/epichlorohydrin reaction in the presence of a Lewis acid catalyst. In this case, the alcohol is usually treated with a slight excess of epichlorohydrin. Examples of Lewis acid catalysts which may be used are boron trifluoride, or a complex thereof, or stannic chloride. The Lewis acid process has the disadvantage that the glycidyl products obtained have an undesired, very high chlorine content.

We have now found that by combining two known techniques, surprisingly the disadvantages of each technique are eliminated and an improved method is achieved for the production of glycidyl ethers from the reaction of primary or secondary alcohols with epichlorohydrin.

Accordingly, the present invention provides a process for the production of glycidyl ethers, comprising A) reacting epichlorohydrin with a molar excess of an aliphatic or cycloaliphatic primary or secondary alcohol, in the presence of a Lewis acid catalyst; optionally B) dehydrochlorinating the product so obtained; and C) reacting the product from step A) or B) with a molar excess of epichlorohydrin in the presence of alkali and a phase transfer catalyst, and isolating the glycidyl ether product so obtained.

The amount of alcohol reactant used in step A) preferably ranges from 1.1 to 5, especially from 1.3 to 2.2 molar equivalents per molar equivalent of epichlorohydrin used.

While monohydric alcohols may be used in step A), e.g. a straight or branched C1–C12 primary or secondary aliphatic monohydric alcohol such as methanol, ethanol, n-propanol, isopropanol, 2-ethyl-1-hexanol, n-hexanol, n-octanol, n-decanol or n-dodecanol, preferably the alcohol reactant contains two or more hydroxyl groups per molecule.

Preferred polyhydroxy reactants are those having the formula (I):

I wherein m is an integer from 2 to 10, preferably 2 to 6 and Q is an m-valent aliphatic, cycloaliphatic or araliphatic residue. When Q is a divalent residue, it may be, e.g. a straight chain or branched alkylene residue; or a cycloalkylene residue in which the ring may be optionally substituted, e.g. by alkyl groups or interrupted by heteroatoms, e.g. O or S atoms or several cycloalkyl residues may be bonded together, optionally via a bridge member. When Q is trivalent or a higher valency, Q may be an organic residue having aliphatic, cycloaliphatic or araliphatic structural elements. Q may be substituted with functional groups provided that such groups do not inactivate the Lewis acid catalyst and do not undergo competing reactions with epichlorohydrin. Suitable functional groups are, e.g. ester groups as contained in polycaprolactones, and unsaturated groups, e.g. those contained in hydroxyl-terminated polybutadienes or polybutadiene copolymers.

Specific examples of preferred aliphatic diol reactants of formula I include diethylene glycol, triethylene glycol and higher polyoxyethylene glycols; propane-1,2-diol, propane-1,3-diol and higher polyoxypropylene glycols; neopentyl glycol; butane-1,4-diol, and higher poly(oxytetramethylene) glycols; pentane-1,5-diol; hexane-1,6-diol; and octane-1,8-diol.

Examples of preferred aliphatic triols of formula I are 1,1,1-trimethylolpropane, glycerol and 1,1,1-trimethylolethane. Other triols of formula I which are commercially—available and are preferred for use in the present invention include adducts of simple polyols such as glycerol, hexane-1,2,5-triol, hexane-1,2,6-triol or hexane-2,4,6-triol with propylene oxide and/or ethylene oxide.

Tetrafunctional aliphatic alcohols which are preferred include pentaerythritol and 3,3,7,7-tetra(hydroxymethyl)-5-oxanonane.

Preferred higher aliphatic poly-hydroxy compounds include dipentaerythritol, tripentaerythritol, mannitol, sorbitol, polyvinyl alcohol, partially hydrolyzed polyvinyl esters or acetals, and hydroxyalkyl acrylate, methacrylate or itaconate polymers and copolymers.

Preferred cycloaliphatic alcohols of formula I include resorcitol, quinitol, bis(4-hydroxycyclohexyl) methane, 2,2-bis(4-hydroxycyclohexyl)propane, cyclohexanedimethanol and 1, 1-bis(hydroxymethyl) cyclohex-3-one.

Alcohols of formula I containing further functional groups which are preferred include polycaprolactone diols and polyols and derivatives of poly(epichlorohydrin).

The Lewis acid catalyst used in step A) of the process of the present invention may be, e.g. boron trifluoride or a complex thereof or stannic chloride, but is preferably a salt of trifluoromethane sulphonic acid or perchloric acid with a metal of Group IIIA of the Periodic Table of Elements (according to the IUPAC 1970 Convention). Preferably the Group IIIA metal is cerium, ytterbium, yttrium or especially, lanthanum.

The amount of the Lewis acid catalyst present in the alcohol/epichlorohydrin reaction mixture generally ranges from 0.1 to 10 parts by weight, preferably from 0.1 to 2 parts by weight based on 100 parts by weight of the alcohol reactant.

The process according to the present invention is conveniently conducted by firstly heating a mixture of the alcohol reactant and the Lewis acid catalyst, preferably with agitation, until a liquid solution is obtained. When the temperature of the solution reaches a temperature within the range of from 50° C. to 200° C., especially a temperature within the range of from 100° C. to 150° C., the epichlorohydrin is conveniently added, preferably with agitation of the reaction mixture. Any exothermic reaction which occurs may be controlled and the reaction temperature maintained within the preferred limits, by applying external cooling in conventional manner. The epichlorohydrin is preferably added, portionwise, over an extended period e.g. over a period ranging from 10 minutes up to 10 hours. The alcohol/epichlorohydrin reaction is preferably conducted in the absence of an inert solvent.

Preferably, the molar ratio of alcohol reactant to epichlorohydrin ranges from 1.1 to 5.

When the alcohol/epichlorhydrin reaction of step A) is judged to have been completed, the usual time required ranging from 1 to 5 hours, the reaction mixture is cooled, if necessary, to a temperature within the range of from 30° C. to 100° C. Step B) dehydrochlorination of the reaction product may be conducted in conventional manner. Dehydrochlorination may be performed, e.g. by adding to the alcohol/epichlorohydrin addition product, an alkali metal hydroxide, in particular sodium hydroxide or potassium hydroxide, optionally together with a quaternary ammonium halide, e.g. tetramethylammonium chloride or benzyltrimethylammonium chloride, as catalyst. If desired, the dehydrochlorination reaction may be performed in the presence of a solvent e.g. 2-methoxyethanol, isodecanol, ethylene glycol, diethylene glycol, N-methylpyrrolidone, gamma-butyrolactone, benzyl alcohol, dibutyl phthalate, methyl ethyl ketone or toluene. The dehydrochlorinating agent is preferably added portionwise, preferably in solid form, over an extended period, e.g. over a period ranging from 10 minutes to 6 hours.

The dehydrochlorination reaction mixture may be worked up in conventional manner e.g. by washing with water and separating and purifying, e.g. by distillation, the organic phase containing the desired glycidylated alcohol product, or the impure dehydrochlorination reaction product may be used directly in step C) of the present process.

Step C) of the process of the present invention is conveniently carded out by firstly contacting the product from step A) or B) with a molar excess of epichlorohydrin, based on the hydroxyl content of the product of step A) or B), and with a phase transfer catalyst, which is usually added as an aqueous solution. Any such added water may then be removed by conventional means, e.g. by an azeotropic distillation technique. Alkali may then be added, preferably as an aqueous solution and in a gradual manner, with continuous removal of water which is formed and/or is added. On completion of the reaction, the glycidylated product may be isolated in conventional manner, e.g. by filtration and fractional distillation.

The amount of epichlorohydrin used in step C) of the process preferably ranges from 3 to 8, especially from 4 to 6 molar equivalents per molar equivalent excess of the alcohol over epichlorohydrin used in step A) of the process of the present invention.

Alkali materials used in step A) and step B) of the present process may be, e.g. alkali metal hydroxides, in particular sodium hydroxide.

The amount of alkali used in step B) preferably ranges from 0.9 to 1.3 moles per mole of epichlorohydrin used in step A).

If step C) involves, as starting material, the product from step A), the amount of alkali used in step C) preferably ranges from 0.9 to 1.3 moles per mole of hydroxyl used in step A).

If step C) involves, as starting material, the product from step B), the amount of alkali used in step C) preferably ranges from 0.9 to 1.3 per mole excess of alcohol over epichlorohydrin used in step A).

The phase transfer catalyst used in step C) of the process of the present invention may be a tertiary amine or a quaternary ammonium base such as benzyltrimethylammonium hydroxide, but is preferably a tetraalkylammonium halide such as methyltrioctylammonium chloride, methyltridecylammonium chloride and, in particular, tetramethylammonium chloride.

The amount of the phase transfer catalyst used in step C) of the present process generally ranges from 0.1 to 10 parts by weight, preferably from 0.2 to 2 parts by weight, based on 100 parts by weight of the product of step A) of the process of the present invention.

The glycidylated ether epoxide resins obtained according to the process of the present invention may be cured in conventional manner, or they may be used as diluents for other epoxy resins so cured. Curing agents which may be used include aliphatic amines; dicyanamide; aromatic amines such as bis(3-aminophenyl)- and bis(4-aminophenyl) sulphone and bis(4-aminophenyl)methane, which are usually used in conjunction with an accelerator such as a $BF_3$-amine complex; carboxylic acids; or polycarboxylic acid anhydrides such as phthalic anhydride, cyclohexane-1,2-dicarboxylic acid anhydride, methylbicyclo [2,2,1]hept-5-ene-2, 3-dicarboxylic acid anhydride, pyromellitic acid dianhydride or benzophenonetetracarboxylic acid dianhydride.

The present invention also provides cured products, e.g. castings or fibre-reinforced composites, comprising a material obtained by curing a glycidylated ether epoxide resin produced by a process according to the present invention.

The products obtained by the process of the present invention have a higher epoxide value and a lower chlorine content relative to a product obtained by conducting only step A) of the present process, when the molar ratio of epichlorohydrin to alcohol would normally be in the range of 1.0 to 1.2 to 1, and then carrying out step B).

When an alcohol reactant is used which is only slightly soluble in warm epichlorohydrin, both the epoxide value and total chlorine content of the resultant glycidyl compound can be superior to epoxide value and total chlorine content for products obtained by carrying out step A) of the present process, when the molar ratio of epichlorohydrin to alcohol would normally be in the range of 1.0 to 1.2 to 1, and then carrying out step B) or by carrying out step C) using, as reactant, a primary or secondary alcohol.

The pot yield of step C) of the present process is higher than that obtained when step C) is conducted in isolation. Finally, the amount of epichlorohydrin used in the process of the present invention and, consequently, the losses of epichlorohydrin when carrying out the present process, are reduced relative to the process in which step B) is performed in isolation, using the alcohol as starting material which undergoes steps A) or B) and C) in the present invention.

The following Examples further illustrate the present invention.

EXAMPLE 1

Step A) Preparation of Chlorohydrin

Cyclohexanedimethanol (216.0 g, 1.5 mole) is placed in a 3-necked flask equipped with a nitrogen inlet, a stirrer, a thermometer and a condenser. The catalyst, lanthanum trifluoromethanesulphonate (0.8 g), is added and the mixture is stirred, with warming, until the catalyst dissolves. The mixture is heated to 120°–130° C. and epichlorohydrin (185 g, 2.0 mole) is added, over about 1 hour, cooling when necessary. After a further 2 hours at 130° C., the epoxide value of the mixture is zero.

Step B) Ring Closure

Ring closure is carded out by adding NaOH (83.3 g, 2.08 mole) in 10 aliquots, adding the first aliquot as a 50% aqueous solution, at 40°–45° C. over about 1 hour. After stirring for a further hour, the salt is filtered off and washed with toluene.

The resin is stripped at 100° C., under vacuum, to yield a product with an epoxide value of 5.49 mol kg$^{-1}$ and a total chlorine content of 1.5%.

Step C) Glycidylation of Residual Hydroxyl Groups

Some of the resin prepared in step B) (111.4 g=0.35 mole—OH) is placed into a 3-necked round-bottomed flask, equipped for azeotropic distillation, having a reverse Dean & Stark water trap.

Epichlorohydrin (98.1 g, 1.06 mole) is added, together with tetramethylammonium chloride catalyst (0.95 g as a 50% aqueous solution), and the mixture is heated to 55°–60° C., under vacuum, to remove the added water, Sodium hydroxide (15.5 g, 0.39 mole, as a 50% aqueous solution) is added, dropwise, over about 3 hours, with continuous separation of the formed and added water in the trap, maintaining the temperature at 55°–60° C. At the end of the addition process, the reaction is allowed to go to completion for 3.5 hours. The product is filtered and stripped at 100° C., under vacuum, to give a material with epoxide value of 6.91 mol kg$^{-1}$ and a total chlorine content of 1.1%.

EXAMPLE 2

Step A)

Example 1 is repeated, but using 1,4-butanediol (500 g, 5.55 mole) lanthanum triflate (3.0 g) and epichlorohydrin (685 g, 7.41 mole).

Step B)

Ring closure is carried out using NaOH (287.3 g, 7.18 mole) at 25°–30° C., over about 1.5 hours with a 2 hour post reaction time, to give a product with an epoxide value of 7.36 mol kg$^{-1}$ and a total chlorine content of 2.1%.

Step C)

The method of Example 1 is repeated, but using some of the resin prepared from step B) above (100 g=0.403 mole—OH) and reacting this with epichlorohydrin (112 g, 1.21 mole) and NaOH (17.7 g, 0.443 mole) using tetramethylammonium chloride catalyst (1.1 g). Reaction time is about 4 hours at 50°–56° C., with a post-reaction time of 1.5 hours. A product with an epoxide value of 8.76 mol kg$^{-1}$ and a total chlorine content of 2.1% is obtained.

EXAMPLE 3

Example 1 is repeated using cyclohexanedimethanol (78.1 g, 0.543 mole), lanthanum trifluoromethane sulphonate (0.29 g), epichlorohydrin (66.7 g, 0.723 mole) and NaOH (28.1 g, 0.702 mole) but the crude resin, salt and water by-products are left in the reaction vessel after step A). Epichlorohydrin (100.4 g, 1.08 mole) is added, and the formed and added water is removed azeotropically using a reverse Dean and Stark water trap. Tetramethylammonium chloride (1.0 g, as a 50% aqueous solution) is added and the residual alcohol (0.364 mole—OH) is reacted as in step C), Example 1, using NaOH (16.0 g 0.401 mole). A product with an epoxide value of 6.91 mol kg$^{-1}$ and a total chlorine content of 1.4% is obtained.

EXAMPLE 4

Step A)

Example 1 is repeated, but using 3,3,7,7-tetra(hydroxymethyl)-5-oxanonane (300 g, 1.2 mole), lanthanum triflate (1.3 g) and epichlorohydrin (296 g, 3.2 mole).

Step C)

The method of Example 1 is repeated but using some of the chlorohydrin resin prepared from step A) above (100 g=0.258 mole—OH, 0.533 mole chlorohydrin) and reacting this with epichlorohydrin (74.4 g, 0.804 mole) and NaOH (33.3 g, 0.832 mole) using tetramethylammonium chloride catalyst (0.73 g).

A product with an epoxide value of 6.69 mol Kg$^{-1}$ and a total chlorine content of 1.7% is obtained.

EXAMPLE 5

Step A)

Example 1 is repeated but using tris(2-hydroxyethyl)isocyanurate (130.5 g, 0.50 mole), lanthanum triflate (1.3 g) and epichlorohydrin (92.5 g, 1.00 mole) adding the epichlorohydrin over 34 hours.

Step C)

The method of Example 1 is repeated using the resin prepared in step A), epichlorohydrin (277.5 g, 3.0 mole) tetramethylammonium chloride (1.3 g) and adding sodium hydroxide (66 g, 1.65 mole) at 36°–48° C. over 2 hours, with a post-reaction of 14 hours. Water (300 ml) is added. The aqueous layer is discarded and the organic layer washed with 10% aqueous sodium dihydrogen phosphate and the solvent removed by distillation under reduced pressure to yield a liquid product with an epoxide value of 5.05 g mole Kg$^{-1}$ and a total chlorine content of 3.9%.

We claim:

1. A process for the production of a glycidyl ether of an aliphatic, cycloaliphatic or araliphatic primary or secondary alcohol, comprising:
    A) reacting epichlorohydrin with a molar excess of the alcohol in the presence of a Lewis acid catalyst; optionally
    B) dehydrochlorinating the product so obtained; and
    C) reacting the product from step A) or B) with a molar excess of epichlorohydrin in the presence of alkali and a phase transfer catalyst, and then isolating the glycidyl ether product so obtained.

2. A process according to claim 1 in which the amount of alcohol reactant used in step A) ranges from 1.1 to 5 molar equivalent per molar equivalent of the epichlorohydrin used.

3. A process according to claim 2 in which the amount of the alcohol used ranges from 1.3 to 2.2 molar equivalents per molar equivalent of the epichlorohydrin used.

4. A process according to claim 1 in which the alcohol reactant is a straight- or branched chain $C_1$–$C_{12}$ primary or secondary aliphatic monohydric alcohol.

5. A process according to claim 4 in which the aliphatic alcohol is methanol, ethanol, n-propanol, isopropanol, 2-ethyl hexanol, n-hexanol, n-octanol, n-decanol or n-dodecanol.

6. A process according to claim 1 in which the alcohol reactant is a compound of formula I:

$$Q(OH)_m \qquad\qquad I$$

wherein m is an integer from 2 to 10 and Q is an m-valent aliphatic, cycloaliphatic or araliphatic residue.

7. A process according to claim 6 in which m is an integer from 2 to 6.

8. A process according to claim 6 in which the alcohol reactant is an aliphatic diol and is diethylene glycol, triethylene glycol or a higher polyoxypropylene glycol; propane-1,2-diol, propane-1,3-diol or a higher polyoxypropylene glycol; neopentyl glycol; butane-1,4-diol or a higher poly(oxytetramethylene) glycol; pentane-1,5-diol; hexane-1,6-diol; or octane-1,8-diol.

9. A process according to claim 6 in which the alcohol reactant is an aliphatic Idol and is 1,1,1-trimethylolpropane, glycerol, 1,1,1-trimethylolethane, or an adduct of glycerol, hexane-1,2,5-triol, hexane-1,2,6-triol or hexane 2,4,6-diol with propylene oxide or ethylene oxide or propylene oxide and ethylene oxide.

10. A process according to claim 6 in which the alcohol reactant is an aliphatic tetrol and is pentaerythritol or 3,3,7,7-tetra(hydroxymethyl)-5-oxanonane.

11. A process according to claim 6 in which the alcohol reactant is dipentaerythritol, mannitol, sorbitol, polyvinyl alcohol, a partially hydrolyzed polyvinyl ester or acetal or a hydroxy alkyl acrylate, methacrylate or itaconate polymer or copolymer, or a poly(epichlorohydrin).

12. A process according to claim 6 in which the alcohol reactant is a cycloaliphatic alcohol and is resorcitol, quinitol, bis(4-hydroxycyclohexyl) methane, 2,2-bis(4-hydroxycyclohexyl)propane, cyclohexanedimethanol or 1,1-bis(hydroxymethyl)cyclohex-3-one.

13. A process according to claim 1 in which the Lewis acid used in step A) is boron trifluoride or a complex there of, or stannic chloride or a salt of trifluoromethane sulphonic acid or perchloric acid.

14. A process according to claim 13 in which the Lewis acid used in step A) is a salt of trifluoromethane sulphonic acid or perchloric acid with a metal of Group IIIA of the Periodic Table of Elements according to the IUPAC 1970 Convention.

15. A process according to claim 14 in which the metal is lanthanum.

16. A process according to claim 1 in which the amount of the Lewis acid catalyst, present in the alcohol/epichlorohydrin reaction mixture of step A), ranges from 0.1 to 10 parts by weight, based on 100 parts by weight of the alcohol reactant.

17. A process according to claim 1 in which the amount of epichlorohydrin used in step C) of the process ranges from 3 to 8 molar equivalents, per molar hydroxyl equivalent of the product of step B) of the process or per molar excess of the alcohol over epichlorohydrin used in step A) of the process.

18. A process according to claim 1 wherein an alkali metal hydroxide is used in step B) or step C).

19. A process according to claim 18 in which the amount of the alkali used in step B) ranges from 0.9 to 1.3 moles per mole of epichlorohydrin used in step A).

20. A process according to claim 1 in which the amount of alkali used in step C) when the product from step A) is the starting material ranges from 0.9 to 1.3 moles per mole of hydroxyl used in step A).

21. A process according to claim 1 in which the amount of alkali used in step C) when the product from step B) is the starting material ranges from 0.9 to 1.3 moles per mole excess of alcohol over epichlorohydrin taken in step A).

22. A process according to claim 19 in which the amount of alkali used ranges from 0.9 to 1.1 moles.

23. A process according to claim 20 in which the amount of alkali used ranges from 0.9 to 1.1 moles.

24. A process according to claim 21 in which the amount of alkali used ranges from 0.9 to 1.1 moles.

25. A process according to claim 1 in which the phase transfer catalyst used in step C) is a tertiary amine, a quaternary ammonium base or a tetra-alkylammonium halide.

26. A process according to claim 25 in which the phase transfer catalyst is tetramethylammonium chloride.

27. A process according to claim 1 in which the amount of the phase transfer catalyst used in step C) of the process ranges from 0.1 to 10 parts by weight based on the weight of the product of step A) of the process.

* * * * *